(12) United States Patent
Peng

(10) Patent No.: US 7,619,328 B2
(45) Date of Patent: Nov. 17, 2009

(54) WALL MOUNTED COUPLING AND POWER SYSTEM

(75) Inventor: Robin Peng, South Jordan, UT (US)

(73) Assignee: Jupiter IP, LLC, Sandy, UT (US)

( * ) Notice: Subject to any disclaimer, the term of this patent is extended or adjusted under 35 U.S.C. 154(b) by 0 days.

(21) Appl. No.: 11/670,976

(22) Filed: Feb. 3, 2007

(65) Prior Publication Data

US 2007/0207664 A1    Sep. 6, 2007

Related U.S. Application Data

(60) Provisional application No. 60/765,104, filed on Feb. 4, 2006.

(51) Int. Cl.
*H02J 7/00* (2006.01)
*H02G 3/08* (2006.01)
*H05K 5/02* (2006.01)

(52) U.S. Cl. ............... 307/155; 220/3.3; 220/3.92; 361/622; 361/624; 361/731; 361/732

(58) Field of Classification Search ............... 307/155; 220/3.3, 3.92; 361/622, 624; D14/302; D24/231, D24/234
See application file for complete search history.

(56) References Cited

U.S. PATENT DOCUMENTS

D431,902 S  * 10/2000 Mellin .................. D3/203.1

| 6,524,240 B1 * | 2/2003 | Thede ............... 600/300 |
| 6,937,461 B1 * | 8/2005 | Donahue, IV ......... 361/622 |
| 6,979,205 B2 * | 12/2005 | Hoopes et al. ........ 439/76.1 |
| 7,141,736 B2 * | 11/2006 | Plankell ............. 174/50 |
| 7,268,998 B2 * | 9/2007 | Ewing et al. ......... 361/622 |

* cited by examiner

*Primary Examiner*—Albert W Paladini
*Assistant Examiner*—Hal I Kaplan
(74) *Attorney, Agent, or Firm*—Geoffrey E. Dobbin

(57) ABSTRACT

The present invention relates to a system for coupling a vertically oriented electrical device to a wall utilizing an existing electrical recess for support and power. The system electrically couples the device to an existing power system while providing a mechanical coupling for support. In addition, the system provides for vertical adjustments while maintaining the electrical and mechanical coupling. The system generally includes a recess coupling module, a vertical support receptacle, an electrical power system, and at least one electrical device. The vertical support receptacle is coupled to the recess coupling module in a substantially perpendicular manner. The electrical power system is electrically coupled to the electrical system disposed in the existing power recess and distributed across the vertical support receptacle. The at least one electrical device is adjustably coupled to the vertical support receptacle such that it is both mechanically supported and electrically powered.

14 Claims, 7 Drawing Sheets

WALL MOUNTED COUPLING AND POWER SYSTEM

CROSS-REFERENCES TO RELATED APPLICATIONS

The present invention claims priority on earlier U.S. Provisional Application 60/765,104, filed Feb. 4, 2006, and incorporates said earlier Application herein by reference in its entirety.

FIELD OF THE INVENTION

The invention generally relates to support and power systems. In particular, the present invention relates to a system for coupling a vertically oriented electrical device to a wall utilizing an existing electrical port for support and power.

BACKGROUND OF THE INVENTION

Due to rising health care costs and increased public availability of medical information, individuals have begun to monitor their personal health independent of medical professionals. A large number of households currently include at least one health value measuring device such as a scale, blood pressure monitor, heart rate monitor, or body fat analyzer. These devices are used to measure at least one value related to an individual's overall health. For example, a scale is used to measure the body weight of a user. Body weight is often tracked to determine if weight is gained or lost over a particular time period. Likewise, weight may be used to self diagnose degrees of obesity which are known to lead to a variety of health related problems. In addition to elective health monitoring, many individuals are required to measure certain health values as a result of one or more medical conditions. For example, a diabetic must monitor his or her insulin levels to determine when it is necessary to ingest or inject supplemental insulin. Likewise, certain heart related conditions require that a patient regularly monitor his or her blood pressure.

In certain circumstances, medical professionals may be required to routinely measure one or more health values to ensure that a patient is healthy. Often, patients that require consistent measurements must be located in a hospital or medical care facility to allow medical professionals to analyze the values. For example, in certain individuals, rapid increases or decreases in blood pressure may indicate a severe medical condition, which must be treated immediately. If a patient is disabled mentally or physically it may not be practical to accurately and reliably perform these measurements. To address this problem, various companies have designed devices and systems to allow for the remote monitoring of patients. These systems allow participants to measure their values and report them to medical professional via some form of communication device. This enables the medical professional to remotely review the values to determine if further intervention is necessary.

However, the existing systems fail to overcome many of the problems encountered in pursuit of accurate, convenient medical value measurement. Participants and patients are often still required to manually measure one or more values. Participants who are mentally or physically incapacitated will not be able to utilize this type of system because of an inability to operate the measurement equipment. In addition, participants may then be required to record the measured values and transmit information to the doctor. These tasks may also be problematic for certain disabled individuals.

In addition, conventional remote health monitoring systems are directed exclusively for severely unhealthy individuals. These systems are designed exclusively to transmit information to a medical professional for review. Therefore, there is no local interpretation of the measured health values. The only information provided to the patient is the individual measurements of each particular device.

Likewise, conventional systems are prohibitively expensive. Each of the measuring devices is often packaged independently of the overall system, thereby requiring independent power sources, user interfaces, and transmission systems. Thus, a user may be required to operate two or more measurement devices in order to provide the necessary health values for proper assessment. These devices are packaged in a manner that prevents or impedes their disposal in a particular tight location, often requiring independent storage. Further, conventional monitoring systems require an operator to install the communication link between the patient and the medical monitoring professional.

Therefore, there is a need in the industry for a medical monitoring system that may be effectively utilized by both healthy and unhealthy individuals, minimizes physical space, minimizes overall cost, and is capable of reliably recording and monitoring health care value information.

It should also be noted that there is a recent increase in interest in the field of home automation and networking. Commercially available networking components have opened a door to a plethora of remote home control, computer networking, and other automation and control methods. A medical monitoring system can be devised to incorporate these features, becoming not merely just a medical monitoring system but a complete home control console. Such systems can benefit from a modular construction, expanding as needed to incorporate what features an individual user desires.

SUMMARY OF THE INVENTION

The present invention relates to a system for coupling a vertically oriented electrical device to a wall utilizing an existing electrical recess for support and power. The system electrically couples the device to an existing power system while providing a mechanical coupling for support. In addition, the system provides for vertical adjustments while maintaining the electrical and mechanical coupling. The system generally includes a recess coupling module, a vertical support receptacle, an electrical power system, and at least one electrical device. The recess coupling module mechanically interfaces with an existing electrical receptacle in a manner to mechanically support or anchor the remainder of the system. The vertical support receptacle is coupled to the recess coupling module in a substantially perpendicular manner. The electrical power system is electrically coupled to the electrical system disposed in the existing power recess and distributed across the vertical support receptacle. The at least one electrical device is adjustably coupled to the vertical support receptacle such that it is both mechanically supported and electrically powered. The electrical devices to be used may range from medical monitoring devices, electrical control devices (like a light switch), home environment control devices (thermostats, humidity control, security), communication devices, networking nodes, verbal, manual and optical input devices, command computer processors, display units and electrical switches.

These and other features and advantages of the present invention will be set forth or will become more fully apparent in the description that follows and in the appended claims.

The features and advantages may be realized and obtained by means of the instruments and combinations particularly pointed out in the appended claims. Furthermore, the features and advantages of the invention may be learned by the practice of the invention or will be obvious from the description, as set forth hereinafter.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The following description of the invention can be understood in light of the Figures, which illustrate specific aspects of the invention and are a part of the specification. Together with the following description, the Figures demonstrate and explain the principles of the invention. The Figures presented in conjunction with this description are views of only particular—rather than complete—portions of the systems and methods of making and using the port system according to the invention. In the Figures, the physical dimensions may be exaggerated for clarity. The same reference numerals in different drawings represent the same element, and thus their descriptions will be omitted.

DETAILED DESCRIPTION OF THE INVENTION

With reference now to the drawings, the preferred embodiment of the application tool is herein described. It should be noted that the articles "a", "an" and "the", as used in this specification, include plural referents unless the content clearly dictates otherwise.

The present invention relates to a system for coupling a modular electrical device to a wall utilizing an existing electrical recess for support and power. The system electrically couples the device to an existing power system while providing a mechanical coupling for support. In addition, the system provides for vertical and horizontal adjustments while maintaining the electrical and mechanical coupling. The system generally includes a recess coupling module, a support receptacle comprised of a central support module and a plurality of support rails, an electrical power system, and at least one electrical device. The recess coupling module mechanically interfaces with an existing electrical receptacle in a manner to mechanically support or anchor the remainder of the system. The support receptacle is coupled to the recess coupling module in a substantially perpendicular manner. The electrical power system is electrically coupled to the electrical system disposed in the existing power recess and distributed across the support receptacle. The at least one electrical device is adjustably coupled to the support receptacle such that it is both mechanically supported and electrically powered.

It should be noted that, as used in this Application, the term "existing electrical recess" shall refer to any type of recess configured for an electrically related application. For example, in a residential building, a face plate and toggle switch may be removed to expose an existing electrical recess. Other existing electrical recesses include but are not limited to recesses designed to accommodate electrical outlets, phone jacks, cable connectors, Ethernet outlets, dimmer switches, security, intercom, etc.

Figure 1:
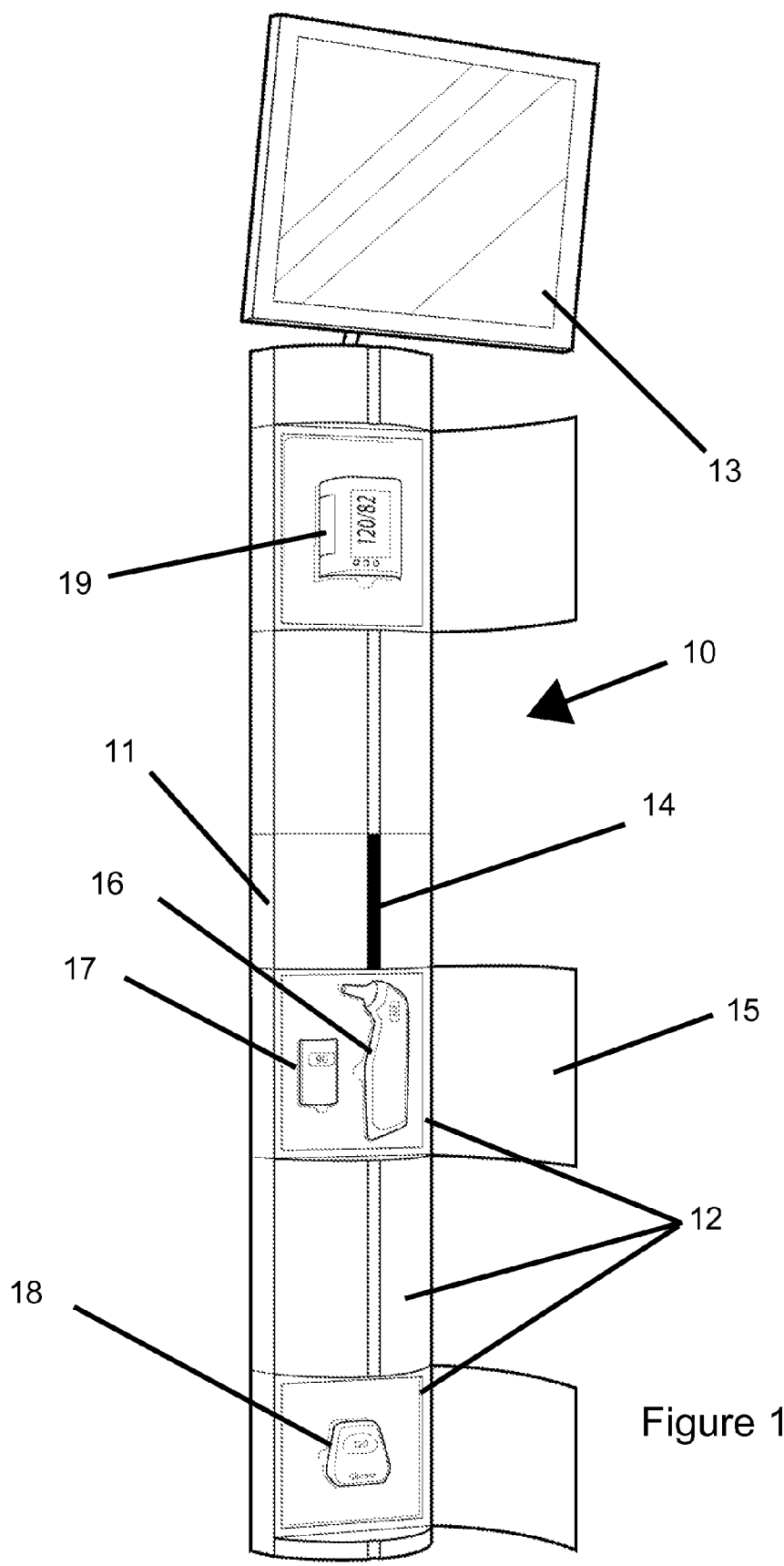
FIG. 1 is a perspective view of one embodiment of the present invention.
Figure 5:
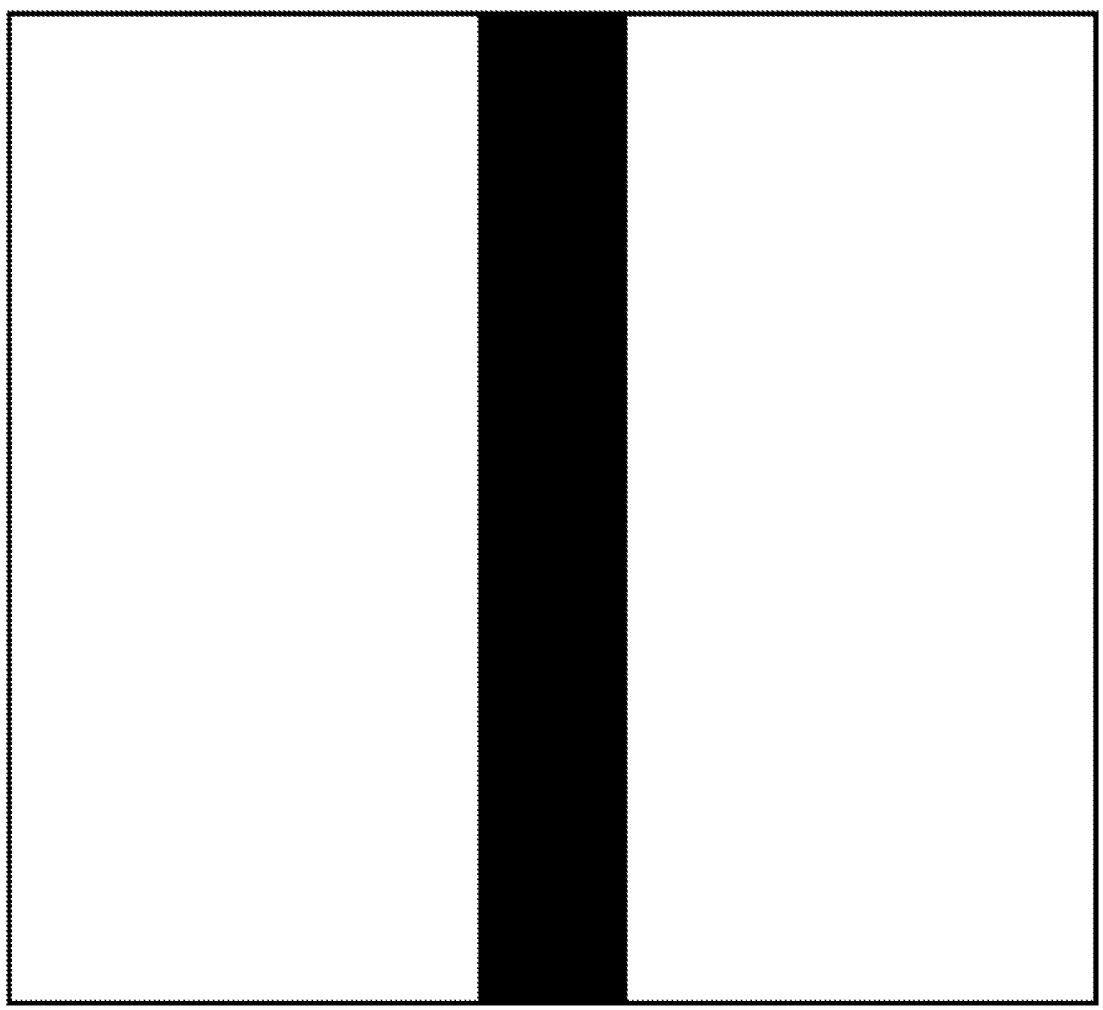
FIG. 5 is a front plan view of the central support module depicted in FIG. 1.
Figure 6:
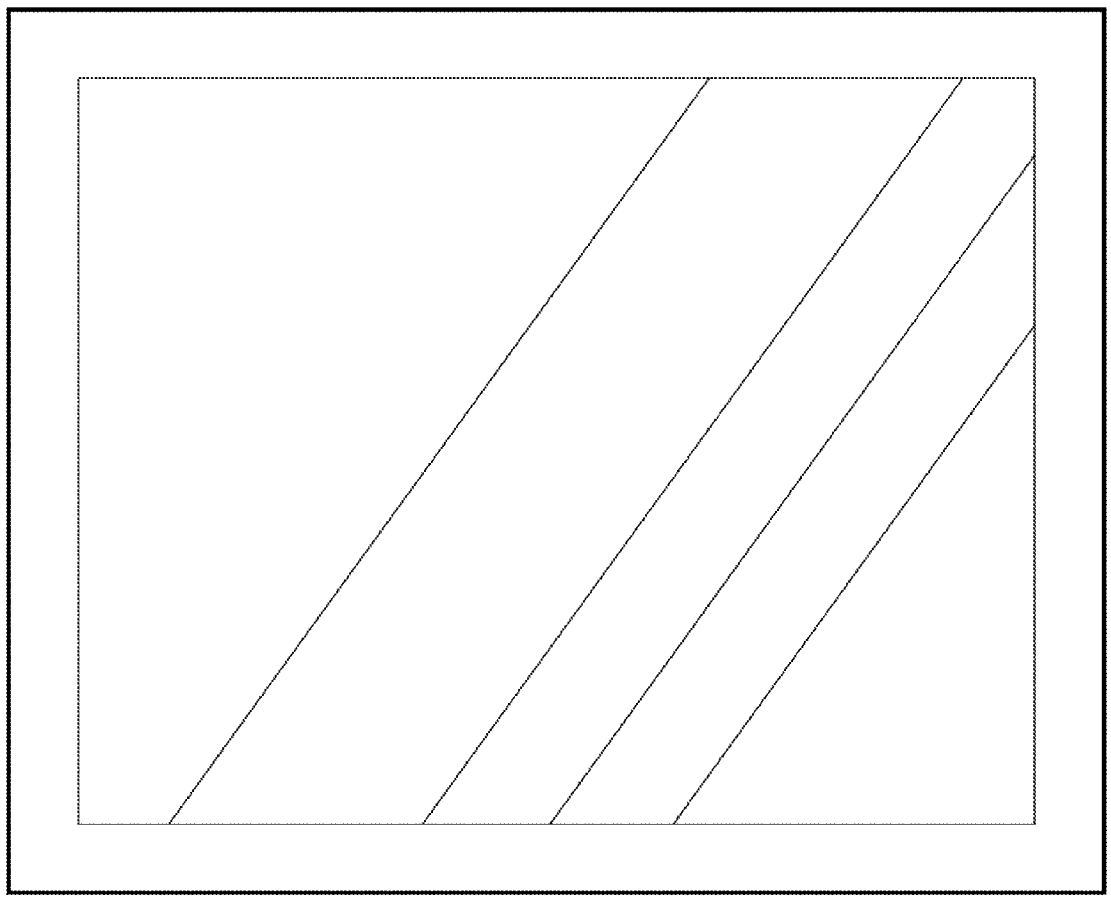
FIG. 6 is a front plan view of an LCD screen depicted in FIG. 1.
Figure 7:
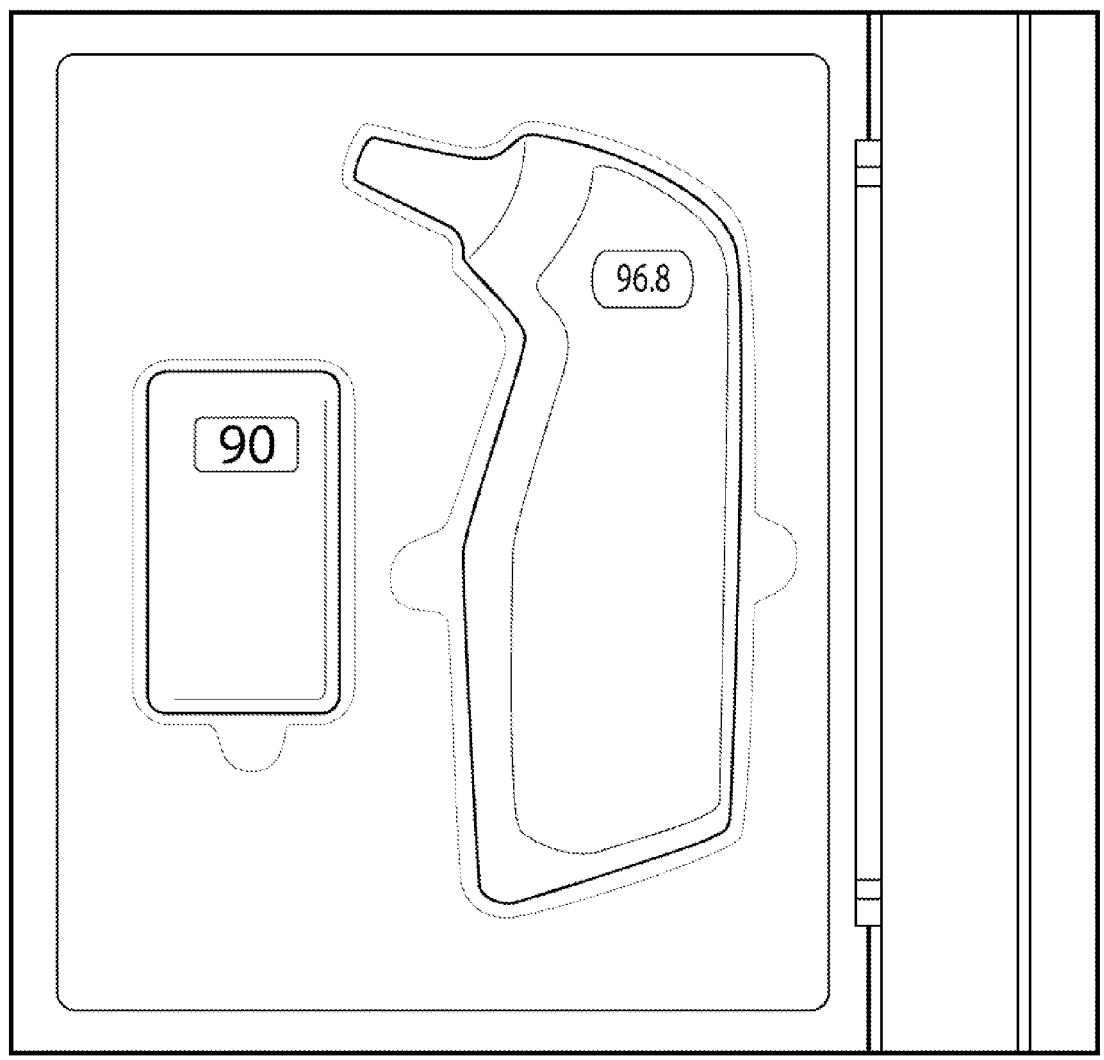
FIG. 7 is a front plan view of one of the system modules depicted in FIG. 1.

Reference is initially made to FIG. 1, which illustrates a perspective view of one embodiment of the system in accordance with the present invention. As illustrated, the monitoring system 10 is mounted and supported in an orientation substantially flush with a wall. This configuration is accomplished with the coupling system described below. The system generally comprises a central support module 11 with a plurality of system modules 12 mounted thereon. In FIG. 1, the modules are illustrated in a vertical orientation, but this does not foreclose the possibility of horizontal orientation or a combination of both. At the top of the system 10, is a view screen 13, which may be either a conventional LCD screen or may be a touch screen, for displaying instructions, results and recommendations, and possibly receiving input. The central support module 11 may feature an electrical device, such as some form of control or device like motion sensitive light switch 14 illustrated in FIG. 1. The design depicted is a digital, touchless electrical switch, issued as U.S. Pat. No. 7,115,856, on Oct. 3, 2006, this Patent is hereby incorporated by reference. System modules 12 generally contain medical equipment and other devices necessary for function of the system. The types of devices can include any conceivably useful electrical device, ranging from medical to home environmental control to communications and beyond. These devices may be enclosed behind a door 15 for protection, or may be exposed, like light switch 14. As an illustration, the open system modules 12 contain medical devices, such as a pulse oximeter 17, ear thermometer 16, glucose monitor 18, and blood pressure reader 19. Close-up views of the central support module 11, screen 13, and the module containing the oximeter 17 and thermometer 16 are provided in FIGS. 5-7 respectively. With a wide variety of devices to choose from, the system may be integrated for any purpose desired by a user dependant on the selected devices. While this Application illustrates the invention with medical devices, usefulness can include home environmental control, networking and information display, security, and combinations of these purposes (i.e. home health care and environmental control) by combining different modules.

Figure 2:
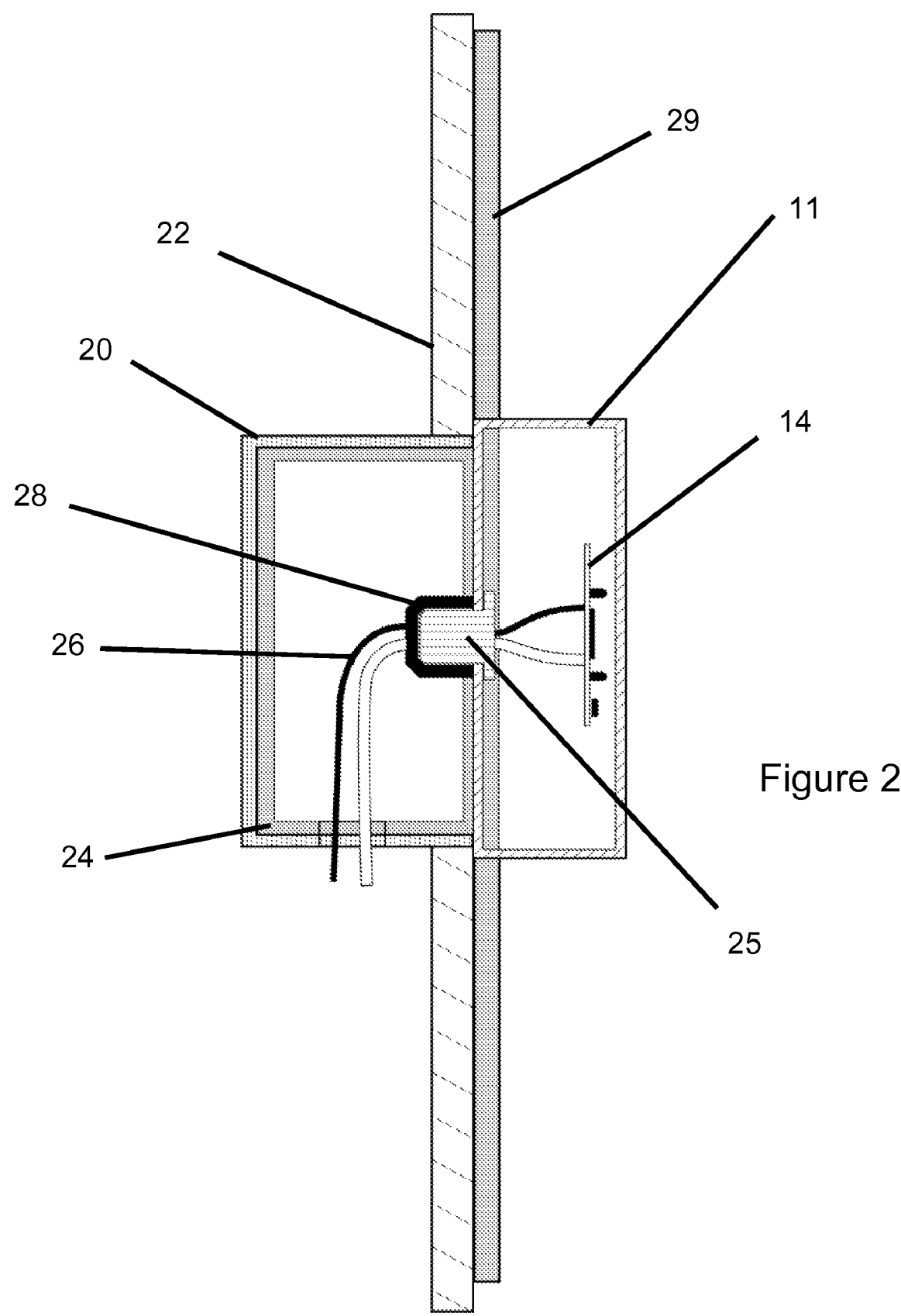
FIG. 2 is a sectional view of a central module according to the present invention mounted in a wall receptacle.

Reference is next made to FIG. 2, which illustrates a cross-sectional view of an existing electrical receptacle 20 with the central support module 11. Various shapes, sizes, and electrical configurations of existing electrical recess have been contemplated by the present invention, though a standard rectangular recess is depicted. The existing electrical receptacle 20 is generally a three dimensional recess in a wall 22 or surface that provides an electrical interface. Central support module 11 has a support structure, a recess coupling module 24 designed to fit within the receptacle 20. The recess coupling module 24 may be secured within receptacle 20 by any means known in the art, including but not limited to screws, nails, expandable anchors, etc. The whole system may obtain additional support by the addition of a mounting plate (not shown) between the recess coupling module 24 and the central support module 11. Electrical wires 26 are threaded through the receptacle 20 and recess coupling module 24 and join with the central support module 11 at an interface. The interface may be of any kind known in the art, such as the plug 28 and receptacle 25 depicted.

Figure 3:
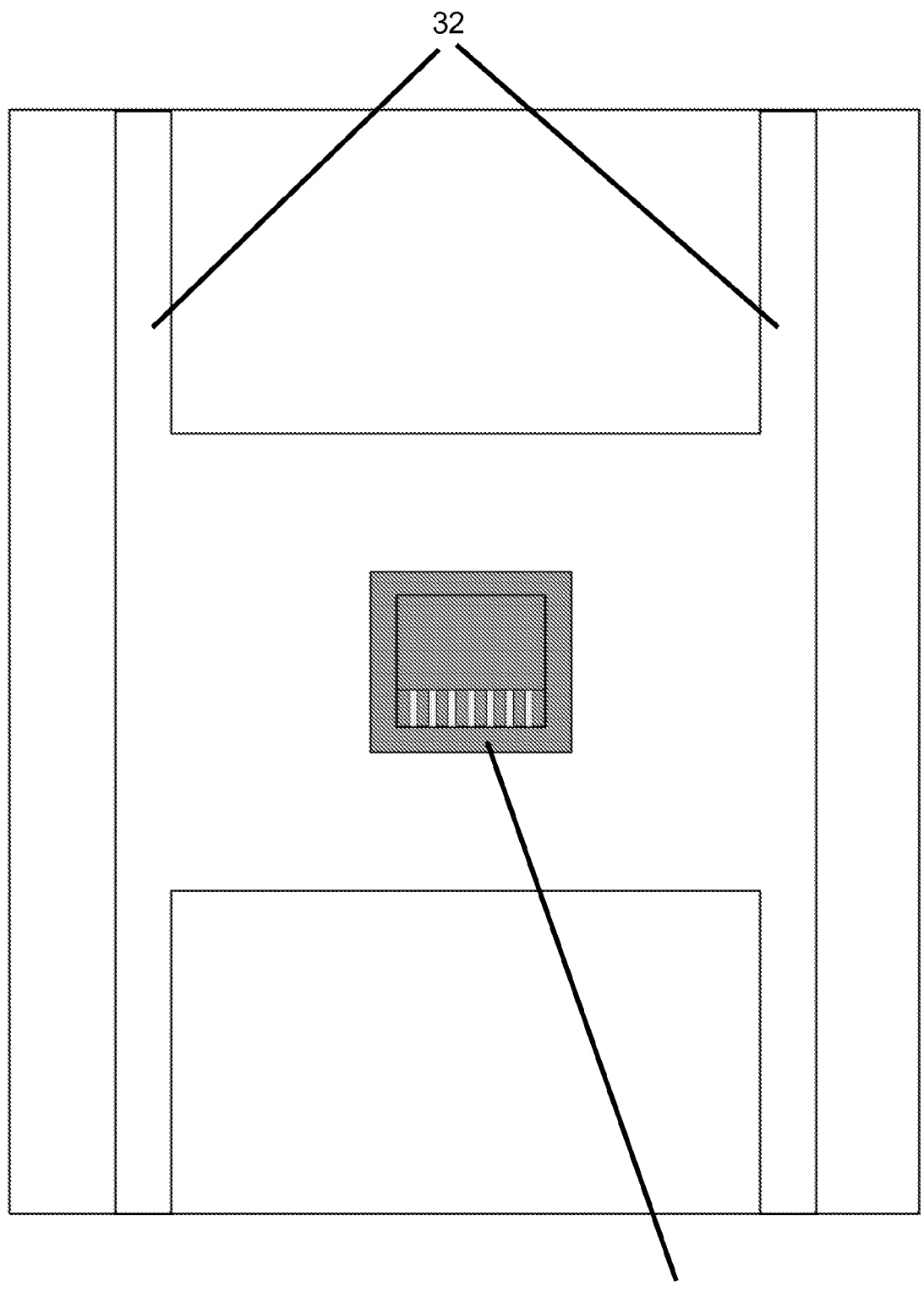
FIG. 3 is a rear elevation of a system module according to the present invention.
Figure 4:
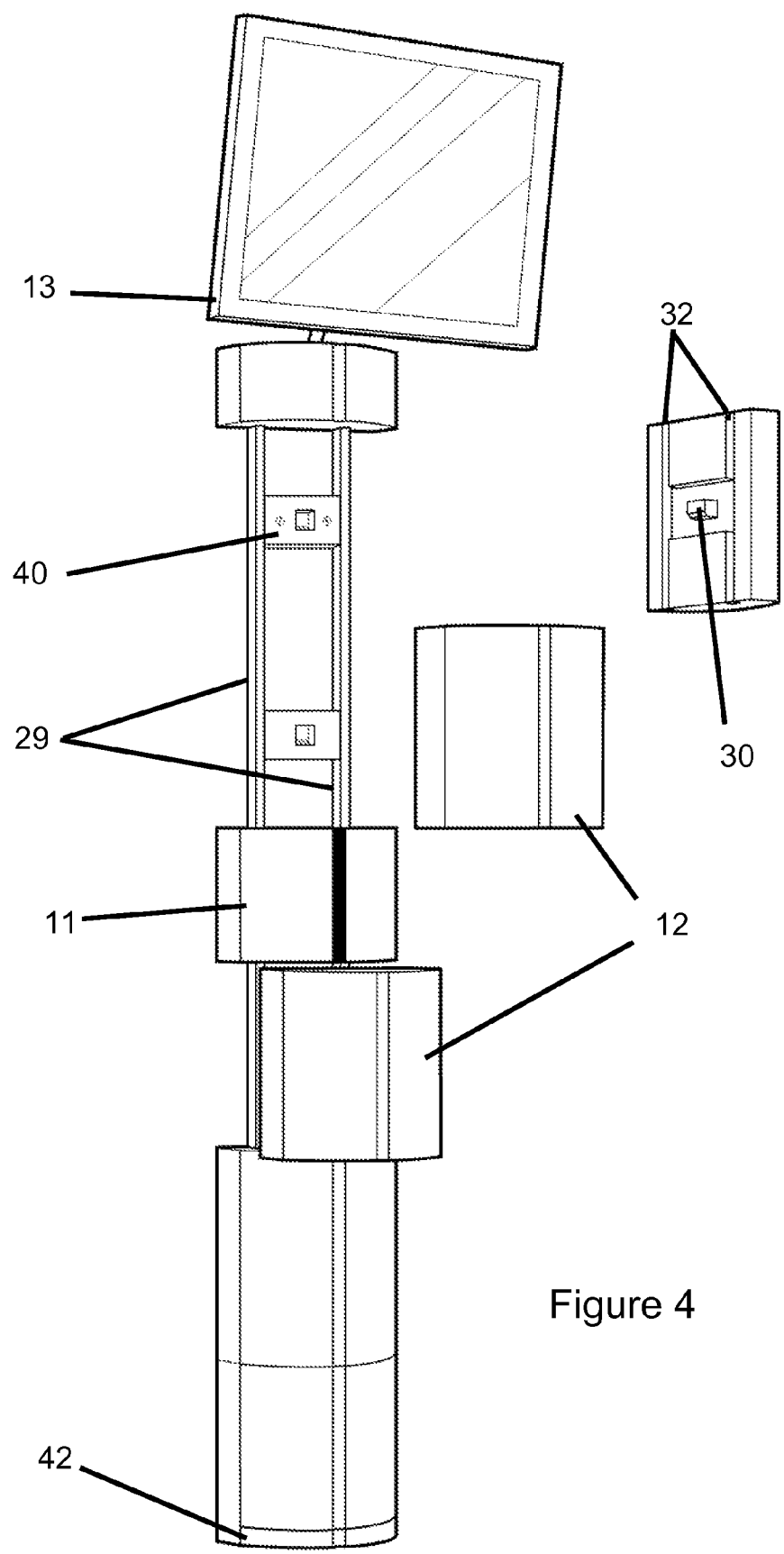
FIG. 4 is a partially exploded view of the system depicted in FIG. 1.

Tracks 29 extending from central support module 11 are also provided for support of other modules. While depicted vertically, tracks 29 may just as easily be horizontal or tracks of both orientations may be provided. At regular intervals along tracks 29, power coupling interfaces 40 are provided (FIG. 4). These interfaces 40 act as a transverse support for the tracks 29 and, therefore, add to the stability of the system. Power and communications are routed from the central support module to each power coupling interface 40. Connection of system modules 12 is accomplished by mounting them on the tracks 29, via mating grooves 32, over the interfaces 40, the rear structure of the modules 12 being shown in FIGS. 3 and 4. Additional support is provided as the rear of each module is designed to encompass the structure of an entire power coupling interface 40. Power coupler 30 mates with interface 40 and provides not only electrical power to the system modules 12, but also provides communication between the system modules 12 and the central support module 11. Communication between the system and a larger network, be it a home network or some other communication system, may be accomplished through a physical dedicated network interface or communication may occur over the power lines of the home, according to what is known in the art or later discovered.

The system may be expanded, being limited only by space available where the system is eventually mounted. The rails 29 and associated power systems may be either extended with more rails 29 or capped with a finalizing cover structure 42 or a finalizing module, such as the screen 13. In so doing, a final product may be provided the user.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A system for adjustably coupling electrical devices to a structure utilizing an existing electrical recess comprising:
   a. A support system, further comprising a plurality of elongate, generally parallel support bars and a recess coupling module configured to mechanically interface with an existing electrical recess to provide structural support for the system, the at least one elongate support bar being substantially aligned with a wall surface and in an orthogonal relationship with the recess coupling module, the support system being mostly disposed outside the electrical recess and;
   b. an electrical power system coupled to an existing electrical power system disposed within the existing electrical recess and distributed across the support system, creating a plurality of additional electrical access points; and
   c. at least one device module adjustably coupled to the support system at an electrical access point such that it is both mechanically supported and electrically powered, the at least one device module supporting and powering at least one electrical device.

2. The system of claim 1, wherein the existing electrical recess is a recess for an alternating current electrical outlet.

3. The system of claim 1, wherein the existing electrical recess is a recess for a toggle switch.

4. The system of claim 1, wherein the at least one electrical device includes a plurality of health care related measurement modules and a display screen.

5. The system of claim 4, wherein the at least one electrical device further includes a communication device.

6. The system of claim 1, wherein the at least one electrical device is selected from the list of electrical devices consisting of: a display device, a medical measurement input device, a networking device, a computer processor, an electrical control device, a climate control device, a communication device, a video input device, a lighting control device, an audio input device, and a manual input device.

7. The system of claim 6, the at least one electrical device being a plurality of electrical devices.

8. The system of claim 1, the at least one electrical device being a plurality of electrical devices.

9. The system of claim 1, wherein the electrical power system further includes one or more electrical communication lines distributed across the support system.

10. The system of claim 1, wherein the recess coupling module includes:
    a. a three-dimensional structure shaped to fit within the existing electrical recess; and
    b. a central support module, containing an electrical device, coupled to the three-dimensional structure and disposed external to the existing electrical recess, from which the plurality of elongate support bars extend.

11. The system of claim 10, wherein the three-dimensional structure is shaped to substantially match the shape of the existing electrical recess so as to three-dimensionally key in to the existing electrical recess.

12. The system of claim 10, the support system also supporting and providing power for at least one additional electrical device, said additional device being supported along the wall surface, external the electrical recess.

13. The system of claim 10, wherein the at least one electrical device is selected from the list of electrical devices consisting of: a display device, a medical measurement input device, a networking device, a computer processor, an electrical control device, a climate control device, a communication device, a video input device, a lighting control device, an audio input device, and a manual input device.

14. The system of claim 13, the at least one electrical device being a plurality of electrical devices.

* * * * *